(12) United States Patent
Vos et al.

(10) Patent No.: US 10,982,849 B2
(45) Date of Patent: *Apr. 20, 2021

(54) PROCESS FOR THE CONVERSION OF BIOMASS OF PLANT ORIGIN, AND A COMBUSTION PROCESS

(71) Applicant: NEWFOSS HOLDING B.V., Uden (NL)

(72) Inventors: Dirk Jan Vos, Opperdoes (NL); Simon Rustenburg, Opperdoes (NL)

(73) Assignee: NEWFOSS HOLDING B.V., Uden (NL)

( * ) Notice: Subject to any disclaimer, the term of this patent is extended or adjusted under 35 U.S.C. 154(b) by 36 days.

This patent is subject to a terminal disclaimer.

(21) Appl. No.: 16/219,939

(22) Filed: Dec. 13, 2018

(65) Prior Publication Data

US 2019/0120487 A1 Apr. 25, 2019

Related U.S. Application Data

(63) Continuation of application No. 13/814,823, filed as application No. PCT/NL2011/000058 on Aug. 11, 2011, now Pat. No. 10,190,769.

(30) Foreign Application Priority Data

Aug. 19, 2010 (NL) ..................... 1038175

(51) Int. Cl.
| | |
|---|---|
| *C10L 5/44* | (2006.01) |
| *C12P 1/00* | (2006.01) |
| *C12P 7/08* | (2006.01) |
| *C12P 19/04* | (2006.01) |
| *C08B 1/00* | (2006.01) |
| *D21C 5/00* | (2006.01) |
| *F23G 5/04* | (2006.01) |
| *F23G 5/02* | (2006.01) |
| *F23G 7/10* | (2006.01) |

(52) U.S. Cl.
CPC .............. *F23G 5/04* (2013.01); *C10L 5/44* (2013.01); *C10L 5/442* (2013.01); *C10L 5/445* (2013.01); *C12P 19/04* (2013.01); *D21C 5/005* (2013.01); *F23G 5/02* (2013.01); *F23G 7/10* (2013.01); *D21C 5/00* (2013.01); *F23G 2209/262* (2013.01); *F23G 2900/50208* (2013.01); *Y02E 50/10* (2013.01); *Y02E 50/30* (2013.01); *Y02P 20/133* (2015.11)

(58) Field of Classification Search
None
See application file for complete search history.

(56) References Cited

U.S. PATENT DOCUMENTS

| | | |
|---|---|---|
| 7,098,009 B2 | 8/2006 | Shanmugam et al. |
| 2005/0178053 A1 | 8/2005 | Kleedorfer et al. |
| 2005/0250192 A1 | 11/2005 | Shanmugam et al. |
| 2007/0098009 A1 | 5/2007 | Du et al. |
| 2009/0061495 A1 | 3/2009 | Beatty et al. |
| 2010/0317079 A1 | 12/2010 | Lesperance et al. |
| 2011/0089271 A1 | 4/2011 | Werner |

FOREIGN PATENT DOCUMENTS

| | | |
|---|---|---|
| DE | 10 2010 027 542 | 11/2011 |
| EA | 000660 B1 | 12/1999 |
| EA | 200970415 A1 | 12/2009 |
| EP | 0055790 | 1/1981 |
| RU | 2 432 368 C2 | 7/2006 |
| RU | 2008 106 242 A | 7/2006 |
| UA | 34477 C2 | 11/2008 |
| WO | 94/23071 | 10/1994 |
| WO | 96/28400 | 9/1996 |
| WO | WO 2006/059316 | 6/2006 |
| WO | 2007/009463 A2 | 1/2007 |
| WO | 2008/073186 A2 | 6/2008 |
| WO | 2008/151417 | 12/2008 |

OTHER PUBLICATIONS

International Search Report for PCT/NL2011/000058 dated Sep. 22, 2011.
Y. Chen et al., "Ensiling Agricultural Residues for Bioethanol Production", Applied Biochemistry and Biotechnology, The Humana Press, Inc., vol. 143, Jan. 1, 2007, pp. 80-92.
M. Thomsen et al., "Pretreatment of Whole-Crop Harvested, Ensiled Maize for Ethanol Production", Applied Biochemistry and Biotechnology, The Humana Press, Inc., vol. 148, No. 1-3, Mar. 1, 2008, pp. 23-33.
A-S. Nizami et al., "Review of the Integrated Process for the Production of Grass Biomethane", Environmental Science & Technology, vol. 43, nr. 22, Nov. 2009, pp. 8496-8508.
D N. Thompson et al., "Effect of Additions on Ensiling and Microbial Community of Senesced Wheat Straw", Applied Biochemistry and Biotechnology, Apr. 2005, vol. 121, pp. 21-46.
ECN rapport ECN C 1 050, titled "Cascadering van maaisel", by J. van Doorn, E.R.P. Keijser and H.W. Elbersen (Energy Centrum Nederland (E.C.N.), Westduinweg 3, NL-1755ZG Petten, the Netherlands (Labeled D7 and D8 (English translation).
M J Waites, et al., "Industrial Microbiology. An Introduction", Blackwell Science Ltd., Oxford, 2001, ISBN 0-632-05307-0, pp. 32-36, 94-107, 240 (labeled D12).

(Continued)

Primary Examiner — Soren Harward
Assistant Examiner — Paul D. Pyla
(74) Attorney, Agent, or Firm — Nixon & Vanderhye P.C.

(57) ABSTRACT

The invention provides a process for the conversion of biomass into a biomass product which is suitable for use as a fuel. The biomass is of plant origin and comprises microorganisms naturally occurring in the biomass. The process comprises—preparing a slurry by dispersing the biomass comprising the naturally occurring microorganisms in an aqueous liquid, maintaining the slurry at conditions suitable for aerobic digestion by the microorganisms to obtain a slurry comprising the biomass product as a dispersed solid phase, and—recovering the biomass product. The recovering comprises washing and drying the biomass product. The invention also provides a combustion process.

17 Claims, No Drawings

(56) References Cited

OTHER PUBLICATIONS

Screen shot of "Cascadering Van Maaisel" dated Mei 2001 with date stamp Jun. 6, 2012, obtained from the website http://www.biorefinery.nl/fileadmin/biorefinery/docs/cascadering_maaisel.pdf (Labeled D10).
ECN: Publicaiteies web shot printed May 18, 2012 from website http://www.ecn.nl (Labeled D9).
Internet Archive Wayback Machine printed May 18, 2012 http://fwww.biorefinervnllfileadmin/biorefinerv/docs/cascadering maaisel.pdf from website http://www.archive.org (Labeled D11).
E. Postmes, H. Guldemeester, "Handboek HACCP", 1995, p. 40-46.
Silage, Wikipedia, the free encyclopedia, http://en.wikipedia.org/w/index.php?title-Silage&oldid-375356392, printed Sep. 14, 2013.
Ye et al, "Properties of medium density fiberboards made from renewable biomass", Bioresource Technology 98 (2007) 1077-1084.
Filya I., "The effect of Lactobacillus buchneri, with or without homofermentative lactic acid bacteria, on the fermentation, aerobic stability and ruminal degradability of wheat, sorghum and maize silages" Journal of Applied Microbiology 2003, 95, 1080-1086.
Hendriks et al "Pretreatments to enhance the digestibility of lignocellulosic biomass" Bioresource Technology 100 (2009) 10-18.
European Office Action dated Nov. 19, 2014, issued in connection with European Application No. 11 741 698.2.
Schaub et al, 1996, Trends in Food Science & Technology, 7, 263-268.
Fraiha et al, 2011, Ciênc. Tecnol. Aliment., Campinas, 31, 167-171.

PROCESS FOR THE CONVERSION OF BIOMASS OF PLANT ORIGIN, AND A COMBUSTION PROCESS

This application is a continuation of commonly owned copending U.S. application Ser. No. 13/814,823, filed Feb. 7, 2013, (now U.S. Pat. No. 10,190,769), which is the U.S. national phase of International Application No. PCT/NL2011/000058 filed Aug. 11, 2011 which designated the U.S. and claims priority to NL 1038175 filed Aug. 19, 2010, the entire contents of each of which are hereby incorporated by reference.

The present invention relates to a process for the conversion of biomass wherein the biomass is of plant origin. The invention also relates to a combustion process which combustion process comprises obtaining a biomass product from a biomass of plant origin, and combusting the biomass product.

The production of renewable energy has been the subject of numerous studies during past decades. Renewable energy may come in various forms, for example in the form of biomass, in particular biomass of plant origin. Biomass of plant origin may be combusted, directly yielding energy in the form of heat, or it may be converted into convenient energy carriers, for example combustible liquids, such as hydrocarbons or alcohols, and combustible gasses, such as methane.

The handling and conversion of biomass of plant origin, however, is difficult because of its physical characteristics, in particular morphology, and because the biomass comprises components which disturb or are harmful in combustion or conversion processes. Undesirable components of biomass of plant origin comprise, for example, carbohydrates, chlorides, alkali metal and alkaline earth metal salts, in particular potassium, calcium and magnesium salts, ammonium salts, nitrogen and sulfur in a form bound to peptides or proteins, ash precursors, and water. Unpleasant odours may affect the environment when handling the biomass, in particular when drying or when combusting the biomass.

Many attempts have been made to treat biomass in order to bring it into a form suitable for the production of energy or energy carriers. Such treatments included steps, such as
 grinding, cutting, milling, or other mechanical treatment aiming at particle size reduction;
 extrusion, pressing or heat treatment aiming at destruction or opening of the biomass' cell structure, or removal of water;
 extensive heating or roasting, aiming at melting or pyrolysis, yielding fuels, such as charcoal, tar or gas; and
 treatment with strong acid or strong base, or oxidizing agents, aiming at conversion of the biomass' lignocellulosic components and making them digestible by enzymes.

A process for the conversion of mown grass is known from ECN report ECN-C-1-050, titled *"Cascadering van maaisel"*, by J. van Doorn, E. R. P. Keijser and H. W. Elbersen (Energy Centrum Nederland (E.C.N.), Westduinweg 3, NL-1755ZG Petten, The Netherlands). The known process comprises the steps of
 treating the mown grass by extrusion, or by steam treatment and extrusion,
 soaking the mown grass so treated in water, and
 recovering from the resulting mixture a solid phase, yielding a grass product.

According to the ECN report, the purpose of treating the mown grass by extrusion, or by steam treatment and extrusion, is destroying the grass' cell structure, so that components present within the cell structure are made accessible to extraction during the soaking.

The known process alleviates only some of the difficulties associated with the handling and conversion of biomass of plant origin. In particular, it is stated that the removal of nitrogen is at most 50% complete, while sometimes hardly any nitrogen is removed, and that insufficient removal of nitrogen is likely caused by the fact that mown grass species tested were not processed while fresh, but only after ageing. Removal of moisture from the grass product is stated to be insufficient, likely necessitating an additional drying step. A problem associated with the known process is that steps of extrusion and steam treatment are energy intensive.

The present invention provides a process for the conversion of biomass into a biomass product which is suitable for use as a fuel, wherein the biomass is of plant origin and comprises microorganisms naturally occurring in the biomass, which process comprises
 preparing a slurry by dispersing the biomass comprising the naturally occurring microorganisms in an aqueous liquid,
 maintaining the slurry at conditions suitable for aerobic digestion by the microorganisms to obtain a slurry comprising the biomass product as a dispersed solid phase, and
 recovering the biomass product.

The process of the invention comprises recovering from the slurry a solid phase, yielding the biomass product. The process of the invention may additionally comprise recovering from the slurry a liquid phase, yielding a biomass extract.

In an embodiment of the process of the invention, the aqueous liquid may be water. In another embodiment of the process of the invention, the aqueous liquid may comprise at least a portion of the biomass extract which was obtained previously in the process of the invention.

The present invention also provides a combustion process, which combustion process comprises the steps of
 preparing a slurry by dispersing a biomass in an aqueous liquid, wherein the biomass is of plant origin and comprises microorganisms naturally occurring in the biomass,
 maintaining the slurry at conditions suitable for aerobic digestion by the microorganisms to obtain a slurry comprising a biomass product as a dispersed solid phase, and
 combusting the biomass product.

It has been found that the invented process is energy efficient and environmentally friendly in that it employs mild conditions, and it allows the use of recycle streams. The invented process is efficient in the removal of undesirable components from the biomass. For example, carbohydrates, such as mono- or disaccharides, alkali metal and alkaline earth metal salts, in particular potassium, calcium and magnesium salts, ammonium salts, chlorides, other salts, sulfur and nitrogen, and combinations thereof can be removed to a high degree. Further, the morphology of the biomass product is such that liquids, for example biomass extract or water, can be removed relatively easily from the biomass product, which also adds to the efficiency of the process, in particular energy efficiency.

Not wishing to be bound by theory, it is believed that the exertion of strong mechanical forces and heat on the biomass by extrusion and steam treatment, as taught by the prior art cited hereinbefore, has a disadvantageous effect on the extractability and processability of the biomass. For example, it may cause denaturing of proteins present in the biomass so that the proteins become virtually insoluble in the aqueous phase and the proteins have, therefore, a strong tendency to stay in the solid phase. It is also thought that the exertion of strong mechanical forces and heat on the biomass may cause particles of the biomass to become too small in size for efficient handling. For example, during the removal of liquid from the biomass by pressing, clogging of particles within the biomass may hinder or prevent a flow of the liquid to leave the biomass. Further, small particles may clog filters and membranes of the equipment which may be used in the recovery of the biomass and liquid products. In respect of these problems, the present invention provides an improvement.

The skilled reader will appreciate that, together with the destruction of the cell structure of the biomass, the exertion of strong mechanical forces and heat on the biomass, as taught by the prior art cited hereinbefore, also causes the destruction of the microorganisms naturally occurring in the biomass, yielding a sterile biomass.

Thus, it is surprising that, while the prior art teaches the destruction of the cell structure of the biomass and the naturally occurring microorganisms of the biomass, the present invention shows that advantageous results can be obtained by using in the process biomass that comprises intact cell structures, living microorganisms and enzymes. Not wishing to be bound by theory, it is believed that microorganisms and/or enzymes associated with the microorganisms are capable of digesting plant components, such as membranes and cell walls, making components of the biomass present within the cell structure accessible to extraction. The extraction involves extraction of components from the biomass into the liquid phase of the slurry. Microorganisms may also be extracted from the biomass into the liquid phase. The extracted components may or may not be subject to further digestion.

The process of the invention employs biomass of plant origin. In general, such biomass comprises lignocellulosic materials. The biomass may comprise aquatic biomass, such as whose, alga, seaweed and duckweed. Preferably, the biomass may comprise land biomass, in particular, forestry waste or agricultural waste. The biomass may be plant parts, such as wood parts, leaves and roots. Examples of suitable land biomass may be wood chips, leaves, reed, straw, corn plants or parts thereof, cabbage plants or parts thereof, sugar beet leaves, line seed plants or parts thereof, bagasse from sugarcane, tomato plants after harvest, rice straw, and, in particular, mown grass, and mixtures thereof. The biomass for use in the invention may or may not have been dried, or the biomass may or may not have been ensilaged.

The biomass for use in the invention may be used as such. However, for easy handling and in view of the specific process equipment in use, it may be desirable to reduce the size of particles of the biomass, for example, by grinding, milling or cutting. Suitably, the largest dimension of the particles may be in the range of from 0.1 cm to 5 cm, more suitably from 0.5 cm to 3 cm. Suitably, the biomass may be mixed with a second biomass, which second biomass may be of plant origin, as well. Such second biomass may not comprise microorganisms naturally present in the biomass. Suitable second biomass may comprise, for example, filter cakes or other secondary product streams obtained in agriculture and/or food processing, such as remnants from vegetable oil extraction processes, and brewing dregs.

The biomass may comprise the microorganisms within its particles, or on the particles surface. Generally, the microorganisms naturally present in the biomass comprise microorganisms which are capable of converting saccharides into lactic acid, lactic acid salts, ethanol or other organic acids, salts or alcohols, typically under mesophylic or psychrophylic growth conditions. Examples of such microorganisms may be bacteria, yeasts and moulds, and combinations. Exemplified species may be lactic acid bacteria such as *Lactobacillus, Lactococcus* and *Streptococcus* species, yeasts such as *Saccharomyces* species and moulds such as *Aspergillus* species.

The process of maintaining the dispersion at conditions suitable for digestion may be a batch process, or it may be a continuous process. In a batch process, the process may be carried out in a tank reactor, for example a vessel or an open tub or container. In a continuous process, the process may be carried out in a tank reactor, or in a plug flow reactor in the form of, for example a tube or a trough. A plurality of reactors may be used, in series, or parallel. The biomass may be dispersed in the aqueous liquid, for example, by adding the aqueous liquid to the biomass. Alternatively, the biomass may be added to the aqueous liquid, or the biomass and the aqueous liquid may be fed simultaneously. Mechanical action, such as gentle stirring, may facilitate forming the slurry. In a continuous process, the process may be carried out by guiding a continuous bed of the biomass through one vessel or through a plurality of vessels comprising the aqueous liquid. Suitably, the weight ratio of the aqueous liquid to the biomass may be in the range of from 1:1 to 50:1, more suitably 2:1 to 20:1, wherein the weight of biomass is taken as the weight of solid matter of the biomass and the weight of aqueous liquid is taken as the total of the weight of aqueous liquid fed and the weight of moisture present in the biomass. The weight of solid matter of the biomass and the weight of moisture present in the biomass are calculated from the moisture content of the biomass.

In an embodiment, the aqueous liquid may be water. The water may be tap water, or it may be distilled water or demineralised water. Water may be selected as the aqueous liquid when the process is carried out for the first time. On the other hand, the water may also comprise at least a portion of water recovered in the process of the invention which has been carried out previously, in which case the aqueous liquid comprises water as a recycle stream. The application of recycle streams improves the process efficiency.

In another embodiment, the aqueous liquid comprises at least a portion of the biomass extract which was obtained in the process of the invention carried out previously. In this embodiment, the aqueous liquid comprises biomass extract as a recycle stream, which improves the process efficiency, as will be explained in more detail hereinafter.

Suitable conditions for digestion by the microorganisms may comprise a temperature of at least 2° C., suitably at least 5° C., more suitably at least 10° C. Typically, the temperature is at most 65° C., more typically at most 40° C., in particular at most 30° C. The pressure is not essential to the process. Suitably the pressure may be in the range of from 0.08 MPa to 0.2 MPa absolute, more suitably in the range of from 0.09 MPa to 0.15 MPa absolute, preferably in the range of from 0.095 MPa to 0.12 MPa absolute. In particular, the pressure may be atmospheric. Sufficient oxygen may naturally be present in the biomass and/or in the aqueous liquid applied in the process supporting aerobic digestion by the microorganisms, and counteracting anaerobic digestion. It may be desirable to gently aerate the slurry. The skilled person will be able to decide on whether or not to apply aeration, and on suitable methods and conditions of aeration. For example, aeration may be effected by stirring using a mechanical stirrer, or by circulating liquid phase or by applying a flow of air or another gas.

The digestion by the microorganisms comprises conversion of mono- and/or disaccharides extracted from the biomass into the liquid phase into lactic acid and/or lactic acids salts. This conversion may result in a decrease of the pH of the liquid phase. Also, during the course of digestion some species of the microorganisms may increase in number, as a result of natural growth, and other species may die because of the decrease in pH. As a result of natural selection, the composition of the microorganisms population may change during the digestion. In the general practice of the invention, the total population may increase in size. Changes in the composition of the liquid phase during digestion may be monitored by measuring pH, refractive index, and/or electrical conductivity or resistivity. Throughout this patent document, pH is defined as pH as measured at 20° C. Digestion may come to an end by depletion of digestible components, for example the mono- and/or disaccharides. Digestion of mono- and/or disaccharides may become slow as a result of the decrease in pH. Although the digestion may become slow, extraction of components from the biomass into the aqueous liquid may continue. If desired, the rate of digestion may be increased by increasing the pH by adding a suitable quantity of base to the slurry, for example aqueous potassium hydroxide, aqueous sodium hydroxide or ammonia. The slurry may be maintained at conditions suitable for digestion by the microorganisms until the digestion has been come to an end, or, more suitably, until the rate at which the composition of the liquid phase changes has become low.

In the embodiment of the invention that the aqueous liquid is water, the pH of the water employed may be essentially neutral, such as in the range of from above 6 to 8.5. More frequently the pH is in the range of from 6.5 to 8.5 or even in the range of from 7 to 8. As explained hereinbefore, in the course of digestion, the pH of the liquid phase will decrease. The pH may decrease until it is in the range of from 5.5 to 7, at which point digestible components may be depleted. In the practice of this embodiment, the slurry may be maintained at conditions suitable for digestion by the microorganisms for a time in the range of from 100 hours to 500 hours, more suitably in the range of from 150 hours to 300 hours.

In the embodiment that the aqueous liquid comprises at least a portion of the biomass extract which was obtained previously, the pH of the aqueous liquid employed may generally be at most 6.7, suitably in the range of from 3 to 6, more suitably in the range of from 4 to 6. In the course of digestion, the pH of the liquid phase may decrease. The pH may decrease until it is in the range of from 3 to 5, more suitably in the range of from 3.2 to 4.5. In the practice of this embodiment, the slurry may be maintained at conditions suitable for digestion by the microorganisms for a time of at least 0.5 hours, more suitable at least 1 hour, in particular in the range of from 0.5 hours to 150 hours, more in particular in the range of from 1 hour to 100 hours. In general, the time may preferably be in the range of from 10 hours to 150 hours, more suitably in the range of from 20 hours to 100 hours. In a continuous process comprising guiding a continuous bed of the biomass through one vessel or through a plurality of vessels comprising the aqueous liquid, the time may preferably in the range of from 0.5 hours to 20 hours, more preferably in the range of from 1 hour to 10 hours, per vessel, for example 2 hours.

The application of biomass extract as a recycle stream, in accordance with the latter embodiment, has several advantages. The application of a recycle stream reduces the quantity of liquid used in the course of multiple batch operations of the process. In the course of such multiple operations, the quantity of microorganisms present in the subsequent recycle streams increases as a result of natural growth and as a result of feeding multiple batches of biomass. Hence, during subsequent operations of the process an increased rate of digestion may be observed. Also, in the course of multiple operations, there may be an increase in the concentration of digestion products, for example lactic acid and lactates, in the subsequent biomass extracts. Further, in the course of such multiple operations, there may be an increase in the concentration of materials which have been extracted from the biomass but have escaped digestion, for example saccharides, alkali metal salts, alkaline earth metal salts, peptides, proteins and aminoacids. The concentration of extracted components and digestion products may increase to such an extent that the biomass extract becomes an economically attractive starting material for further processing. The skilled person will appreciate that the same advantages apply in an analogous manner when the process is carried out as a continuous process.

In the batch operation of the process, the biomass extract obtained in a first operation of the process may be used in from 1 to 6 times (inclusive) subsequent operations of the process. Preferably, the biomass extract obtained in the first operation of the process may be used in from 3 to 5 times (inclusive) subsequent operations of the process. Alternatively, a steady state multiple operation may be reached by bleeding a portion of recycled biomass extract, and replacing that portion by water. In an analogous manner a steady state may be reached in a continuous process.

Any method for solid-liquid separation may be used for recovery of the biomass product and the biomass extract from the slurry, for example sedimentation, filtration or centrifugation. In a typical method, a filter plate or a screen may be employed for this purpose. To this end, the slurry may rest on top of a filter plate positioned near the bottom of a vessel which holds the slurry, of which filter plate the openings are small enough to substantially resist solids of the slurry to pass the filter plate, while biomass extract may pass the filter, in particular under the influence of gravitational force or pumping, leaving the biomass product at the side of the filter plate which is adjacent to the slurry. As an alternative, a screen, in particular an in-line screen, may be employed of which the openings are small enough to substantially resist solids of the slurry to pass the screen and of which screen the openings are small enough to substantially resist solids of the slurry to pass the filter plate, while biomass extract may pass the filter, in particular under the influence of gravitational force or pumping, leaving the biomass product at the side of the screen which is adjacent to the slurry. As yet another alternative, the bottom of the vessel may have one or more drainage slits or drainage channels of suitable dimensions such that biomass extract may pass the drainage slits or drainage channels and leave the vessel, while solids of the slurry substantially remain in the vessel. This process may be facilitated by exerting pressure onto the slurry, for example by pumping, by means of a piston or by pressurising the atmosphere above the slurry. In general, the pressure exerted onto the slurry will be kept low, for example in the range of from 0.0001 MPa to 0.05 MPa, more suitably in the range of from 0.0005 MPa to 0.02 MPa, preferably in the range of from 0.001 MPa to 0.015 MPa. A preferred method of gently exerting pressure onto the slurry is by having floating on top of the slurry a bag containing water, which bag has a size and a shape and is made of a flexible material, for example a plastic or rubber, such that the bag is capable of adapting its shape to the shape of the vessel to completely cover the slurry. If desired, a stack comprising two, three of four bags may be applied. The total height of the one or more bags may typically be in the range of from 0.1 m to 2 m, more typically from 0.2 m to 1.5 m, for example 0.5 m or 1 m. Typically, the vessel is of a cylindrical shape, preferably a circular, elliptic, rectangular or squared cylindrical shape. The vessel may be positioned such that the axis of the cylindrically shaped vessel is in the horizontal or vertical direction.

In the normal practice of the recovery method described in the previous paragraph, it may appear that a portion of the biomass extract tends to remain in the biomass product. In such a case, it may be desirable to remove more of the biomass extract from the biomass product, increasing the solids content of the biomass product. It has been found that this can be achieved effectively and in an energy efficient manner by slowly building up mechanical force onto the biomass product. For example, the biomass product may be charged to a press and the pressure in the press is slowly increased. By slowly increasing the pressure, plugging or clogging within the biomass product may be diminished or prevented, which plugging or clogging would otherwise hinder or prevent biomass extract leaving the biomass product.

Independent of whether or not the biomass product has been subjected to the treatment described in the previous paragraph, the biomass product may be washed to further remove biomass extract. The washing may be carried out as a single washing step. It may be preferred to apply a plurality of washing steps, for example, up to 5 (inclusive) washing steps. Any liquid which is miscible with the biomass extract may be suitable as a washing liquid. Water is a very suitable washing liquid. It is preferred to apply a plurality of washing step in a counter current process. In particular, in the counter current process water is applied as the washing liquid in the last washing step. In a continuous process comprising guiding a continuous bed of the biomass through a plurality of vessels comprising the aqueous liquid, the vessels may be fluidly connected to one another to form a series arrangement of vessels, and a flow of the aqueous liquid may be maintained countercurrently to the movement of the bed of the biomass. In this case, water may be fed to the first vessel in the series arrangement and biomass extract may be withdrawn from the last vessel in the arrangement. The number of vessels in the series arrangement may suitable be from 3 to 6 (inclusive).

Associated with each washing step, the effluent may be separated from the biomass product in a manner similar as the recovery of the biomass product and the biomass extract from the slurry, as described hereinbefore, including the methods of removing biomass extract form the biomass product, as described hereinbefore. Effluents of the one or more washing steps, in particular the effluent of the first washing of multiple countercurrent washing steps, may be added to the biomass extract. Alternatively, effluents may be applied as the aqueous liquid, or as a portion of the aqueous liquid.

The washed biomass product may be dried to reach a low moisture content. A wide range of dryers may suitably be applied, operating at a high temperature or at a low temperature; operating in continuous mode or batch-wise; applying vacuum or operating at overpressure, such as a steam dryer; or with the biomass present as a stacked bed or as a fluidised bed. Drying may be effected, typically, at a temperature of at most 600° C., more typically at most 400° C. Preferably, drying may be effected at a temperature in the range of from 25° C. to 600° C., more typically 30° C. to 400° C. For energy efficiency, the dryer equipment may comprise the dryer, a heating system for heating the biomass product entering the dryer, a condenser and a heat pump system recycling energy set free in the condenser to the heating system. Condensate water obtained from the drying step may be applied elsewhere in the process, for example as washing liquid or a portion thereof, or as the aqueous liquid or a portion thereof. It has been found that the off-gasses of the drying step are low in badly smelling components and low in dust, so that they can be handled easily and they are relatively environmentally friendly. Thus, alternatively, drying may be accomplished by spreading the biomass product on a field for exposure to outside weather conditions, in particular for sun drying. It is an advantage of this invention that, if desired, the biomass product may be left on the field for an extended period of time, for example for weeks or even for months, spread-out or piled-up, without showing noticeable signs of rotting or generation of heat. This represents a convenient method of outdoor storage, as an attractive alternative to ensilage.

The solids content of the biomass product obtained in accordance with this invention may be at least 25% by weight, typically at least 50% by weight, more typically at least 60% by weight, preferably at least 70% by weight, more preferably at least 80% by weight, in particular at least 90% by weight. In the normal practice of this invention, the moisture content of the biomass product may be at most 99% by weight, more frequently at most 95% by weight. The moisture content of the biomass product may be at most 75% by weight, typically at most 50% by weight, more typically at most 40% by weight, preferably at most 30% by weight, more preferably at most 20% by weight, in particular at most 10% by weight. In the normal practice of this invention, the moisture content of the biomass product may be at least 1% by weight, more frequently at least 5% by weight. Throughout this patent document, moisture content is defined as moisture content in % by weight as measured by using ISO 11722, and the content of solid matter is defined as 100% by weight minus the moisture content.

The biomass product obtained in accordance with the invention has a high content of lignocellulosic materials. The biomass product has a low content of alkali metals, alkaline earth metals, nitrogen, phosphates, sulphate, chloride, proteins and saccharides. Typically the biomass product may have a content of potassium of at most 0.1% by weight, more typically at most 0.05% by weight, in particular at most 0.03% by weight, relative to the weight of solid matter. In the normal practice of this invention, the content of potassium is frequently at least 0.001% by weight, more frequently at least 0.005% by weight, relative to the weight of solid matter. Typically the biomass may have a content of chloride of at most 0.1% by weight, more typically at most 0.05% by weight, in particular at most 0.03% by weight, relative to the weight of solid matter. In the normal practice of this invention, the content of chloride is frequently at least 0.001% by weight, more frequently at least 0.005% by weight, relative to the weight of solid matter.

The biomass product is excellently suited as a fuel or starting material for combustion or conversion processes, such as gasification and pyrolysis, because it has a low ash content, a high ash fusion temperature, a low tendency to cause corrosion, and a low tendency to cause emissions of nitrogen oxides and sulfur oxides. The biomass product may be employed as such, or together with another fuel or starting material.

It has been found that the biomass product has a high caloric value. For example, on the basis of the weight of mown grass, more heat can be generated by burning the biomass product obtained from the mown grass by using the invention, compared with the heat which can be generated by burning the methane obtained by anaerobic digestion (fermentation) of the mown grass, even including the heat which can additionally be obtained by burning the digestate coproduced in the fermentation.

The biomass product may be used as a fuel, irrespective of its moisture content and irrespective of whether the biomass product has been dried, or not. Namely, water present in the biomass product may evaporate during the drying process or during the combustion; this is a choice an operator may make. An environmentally friendly option may be outside drying, in particular sun drying, of the biomass product prior to its use as a fuel, as in this case the heat of evaporation of water is supplied by the sun, and will not be at the expense of the heat obtained in the combustion process.

The biomass product obtained in accordance with the invention is also excellently suitable for use as a starting material in an anaerobic digestion for the production of methane gas. The biomass product obtained in accordance with the invention is also excellently suitable for use, for example as a filler material for plastics, concrete or bitumen, or for making board material for building purposes.

The biomass extract obtained in accordance with the invention may have a high content of salts, such as alkali metal salts, alkaline earth metal salts, lactates and chlorides, and lactic acid and neutral organic compounds, such as saccharides. It also has a relatively high content of microorganisms. The biomass extract has a remarkable stability and may be stored for extended periods of time, such as weeks or months. If desired, the biomass extract may be concentrated by removing water. Water may be removed from the biomass extract, for example, by evaporation or by applying reverse osmosis. The water obtained in this manner may be recycled, for example, for use as (a portion of) the aqueous liquid, or for use as a washing liquid.

With or without prior removal of water, as described in the previous paragraph, the biomass extract may be subjected to a separation process, such as membrane filtration. The biomass extract may be separated into, on the one hand, an aqueous effluent comprising salts, such as alkali metal salts, alkaline earth metal salts, lactates and chlorides, and lactic acid and, on the other hand, an aqueous concentrate comprising neutral organic compounds, such as mono- and disaccharides, and proteins. The biomass extract obtained in accordance with this invention behaves favourably in membrane separation techniques, in terms of low membrane fouling and long filtration run times. The aqueous effluent or a portion thereof may advantageously be recycled as a portion of the aqueous liquid. If desired, water may be removed from the aqueous effluent and/or the aqueous concentrate by methods described in the previous paragraph, and, optionally be recycled, for example for use as (a portion of) the aqueous liquid, or for use as a washing liquid.

The invention will be further illustration by means of the following working examples.

EXAMPLE 1

In Accordance with the Invention

A container was provided having inner dimensions of 3 m×2 m×1.7 m (length×width×height), a flat, rectangular, horizontal, concrete bottom and four flat, rectangular, vertical, concrete walls, and having placed therein a solid wooden plank supported by wooden blocks placed on the bottom at regular distances, the plank having been placed such that an open drainage channel (20 cm width and 20 cm depth) was formed at one side of the bottom in the longitudinal direction of the container. The container was charged with 540 kg of mown grass (37% by weight moisture content, representing 200 kg water) and 940 kg of water (a mixture of rain water and tap water) having pH 6.75, electric conductivity 0.62 mS/cm, refraction 0° Brix and temperature 9° C. In order to assist in obtaining and maintaining a slurry of the grass in the liquid phase, liquid phase was circulated by pumping at a rate of 5000 kg/h from the bottom of the drainage channel in one corner of the container onto the upper surface of the mixture of grass and water in the opposite corner of the container. After 1 hour the pH of the liquid phase had reached 6.6, refraction 1° Brix, electric conductivity 4.6 mS/cm, temperature 9.5° C. (Throughout this patent document, values of pH, refraction and electric conductivity are as measured at 20° C.). The circulation of liquid phase was continued.

The next day, this procedure was repeated, yielding a second batch of slurry. After circulating liquid phase for 168 hours the two batches were combined, resulting in the following: a total of about 2960 kg slurry consisting of about 2280 kg of liquid phase and about 680 kg of solid phase, the liquid phase being a slightly foaming, clear, dark brown coloured liquid, and having a fresh sour odour and the following characteristics: electric conductivity 4.8 mS/cm, pH 6.6, refraction 1° Brix, temperature 9° C.

Then circulation of liquid phase was stopped and, instead, liquid phase was pumped into a separate container of similar size. In this manner about 45% by weight of the liquid phase could be separated from the slurry, yielding about 1350 kg of a first lot of biomass extract.

A rubber and nylon-fibre lined bag having dimensions such that the bag fits the horizontal inner dimensions of the container was placed in the container, covering the slurry. Then the bag was filled with tap water and closed. The height of the column of water inside the bag was 50 cm. A second bag of similar dimensions was placed on top of the first bag and filled with tap water until the height of the column of water inside the second bag was 50 cm. Additional liquid phase was drained by pumping from beneath the drainage channel. In this manner about 500 kg of a second lot of biomass extract was obtained.

The biomass product remaining in the container was then washed. To this end, the biomass product was re-dispersed in 1000 kg of tap water and the liquid phase so obtained (1000 kg) was drained by pumping from beneath the drainage channel with the two water filled bags still in place. Washing was repeated two times. The washing effluents were combined and stored for use in Example 2, hereinafter.

10-kg samples of the washed biomass product were transferred into a hydraulic juice press filling the cylinder of the press and subjected to pressing. For each pressing, the pressure inside the press was increased in 2 minutes from 0.1 MPa to 5 MPa, while pressing juice was drained and collected. After pressing the biomass product had a moisture content of 47% by weight. The weight of each of the blocks of biomass product obtained was about 5 kg.

The biomass product blocks where loaded into open containers (1.5 m length, 1 m width, 1 m height), each container having a wooden pallet as a bottom and four wire nettings supported by a metal framework as side walls. The wire nettings possessed 10 cm×10 cm openings for passing drying air. The open containers had no cover. The open containers filled with biomass product blocks were placed in a drying kiln as a stack of three layers of two by three open containers each. The drying kiln was operated as a condenser dryer at temperatures of 45-65° C., for 96 hours. After drying, the biomass product had a moisture content of 10% by weight.

The first lot of biomass extract was processed by means of a membrane filter installation provided with commercially available spirally wound polymer nano-filtration membranes and protective filter candles positioned up-stream relative to the membranes. The membrane filter installation was operated at 2.5 MPa (25 bar) and at a rate of 200 kg/h, producing 70-100 kg/h of permeate and 100-130 kg/h of concentrate. During the operation the concentrate was recycled into the container comprising the biomass extract, and permeate was collected in another, similar container. Accordingly, the concentrate became progressively more concentrated in mainly proteins, mono- and disaccharides, and it became more dark brown and cloudy. The permeate, comprising chlorides, nitrates and other salts and lactic acid, had a water clear appearance.

During the nano-filtration process, the temperature of the concentrate increased slowly from about 10° C. to about 40° C., caused by the supply of energy to the pumping equipment of the membrane filter installation. The higher temperature resulted in 200% more filtration capacity of the process. The membrane filtration appeared to be a very efficient process for the removal of salts and lactic acid from the biomass extract and for concentrating the biomass extract. It is remarkable that the nano-filtration process could proceed with long run times and—with no pre-filtering other than by applying the filter candles—without significant fouling of the filter candles and the membranes.

The permeate was concentrated by removing water by means of reverse osmosis applying a pressure of 7 MPa.

The first lot of biomass extract, the concentrate obtained at the end of nano-filtration process, and permeates obtained at the start and at the end of the nano-filtration process were analysed (see Table I, below; "COD" means chemical oxygen demand). The results depicted in Table I are indicative for a concentration factor of 15-20 for the concentrate, relative to the biomass extract, and that potassium chloride is present in the permeate in a high concentration.

TABLE I

| | Electric conductivity (mS/cm) | pH | Density $d_{20}$ (g/l) | Refraction (° Brix) | KCl content (g/l) | COD (g/l) | Dry matter (% by weight) |
|---|---|---|---|---|---|---|---|
| Biomass extract | 6.52 | 3.83 | 1.002 | 1 | — | 6.5-7.5 | — |
| Concentrate | 104 | 4.4 | 1.072 | 17 | — | 140-150 | 19.5 |
| Permeate at start | 2.3 | 3.9 | — | 0 | 1.0-1.25 | — | — |
| Permeate at end | 11 | 3.7 | — | 1 | 15.0-20.0 | — | — |

— not analysed

EXAMPLE 2

In Accordance with the Invention

Example 1 was repeated with the difference that the container was charged with 1000 kg of the mown grass and then filled with 2000 kg of washing effluent obtained in Example 1, instead of water. After circulating liquid phase for 96 hours, the liquid phase had reached pH 6.0. 1800 kg of biomass extract and 1200 kg of wed biomass product were obtained. After pressing the biomass product had a moisture content of 50% by weight and after drying, the biomass product had a moisture content of 10% by weight. The pressing juice obtained from pressing in the hydraulic juice press (about 200 kg) was collected.

EXAMPLE 3

In Accordance with the Invention

Example 2 was repeated with the difference that, after charging with 1000 kg of the mown grass, the container was charged with 1800 kg of the biomass extract obtained in Example 2 and 200 kg of the permeate obtained in Example 1, instead of the washing effluent obtained in Example 1. After circulating liquid phase for 48 hours, the liquid phase had reached pH 4.2. 1800 kg of biomass extract and 1200 kg of wed biomass product were obtained. After pressing the biomass product had a moisture content of 50% by weight and after drying, the biomass product had a moisture content of 10% by weight.

EXAMPLE 4

In Accordance with the Invention

Example 3 was repeated with the difference that, after charging with 1000 kg of the mown grass, the container was charged with 1800 kg of the biomass extract obtained in Example 3, and 200 kg of the permeate obtained in Example 2, instead of the biomass extract obtained in Example 2, and the permeate obtained in Example 1. After circulating liquid phase for 48 hours, the liquid phase had reached pH 3.8. 1800 kg of biomass extract and 1200 kg of wed biomass product were obtained. After pressing the biomass product had a moisture content of 50% by weight and after drying, the biomass product had a moisture content of 10% by weight.

The invention claimed is:

1. A process for the conversion of biomass into a biomass product, wherein the biomass is of plant origin and comprises microorganisms naturally occurring in the biomass, the process comprising:
   (i) preparing a slurry by dispersing the biomass comprising the naturally occurring microorganisms in an aqueous liquid,
   (ii) maintaining the slurry at conditions suitable for aerobic digestion by the microorganisms to obtain a slurry comprising the biomass product as a dispersed solid phase, and
   (iii) recovering the biomass product, which recovering comprises washing using water as a washing liquid and drying the biomass product.

2. The process as claimed in claim 1, further comprising (iv) recovering from the slurry a liquid phase to yield a biomass extract.

3. The process as claimed in claim 1, wherein the aqueous liquid is water.

4. The process as claimed in claim 3, wherein the water has a pH measured at 20° C. which is in a range of from 6.5 to 8.5, and wherein step (ii) comprises maintaining the slurry at conditions suitable for digestion by the microorganisms for a time in a range of from 100 hours to 500 hours.

5. The process as claimed in claim 4, wherein the pH is in the range of from 7 to 8, and wherein the time is in the range of from 150 hours to 300 hours.

6. The process as claimed in claim 1, wherein the aqueous liquid comprises at least a portion of a biomass extract obtained by additionally recovering from the slurry a liquid phase to yield the biomass extract.

7. The process as claimed in claim 6, wherein the aqueous liquid has a pH as measured at 20° C. which is in a range of from 3 to 6, and wherein step (ii) comprises maintaining the slurry at conditions suitable for digestion by the microorganisms for a time in a range of from 0.5 hours to 150 hours.

8. The process as claimed in claim 7, wherein the pH is in the range of from 4 to 6, and wherein the time is in the range of from 1 hour to 100 hours.

9. The process as claimed in claim 1, wherein the biomass comprises forestry waste or agricultural waste.

10. The process as claimed in claim 9, wherein the biomass comprises mown grass.

11. The process as claimed in claim 1, wherein the naturally occurring microorganisms comprise microorganisms which are capable of converting saccharides into lactic acid or lactic acid salts.

12. The process as claimed in claim 1, wherein the conditions suitable for digestion by the microorganisms comprise a temperature in a range of from 5° C. to 40° C.

13. The process as claimed in claim 12, wherein the temperature is in the range of from 10° C. to 30° C.

14. The process as claimed in claim 1, wherein step (iii) comprises recovering the biomass product from the slurry with a filter plate or a screen while exerting a pressure of from 0.0005 MPa to 0.02 MPa onto the slurry.

15. The process as claimed in claim 1, wherein step (iii) comprises a plurality of washing steps in a counter current process, wherein a last one of the washing steps includes using water as a washing liquid.

16. The process as claimed in claim 1, wherein step (iii) comprises drying the biomass product to achieve a moisture content of the biomass product of at most 20% by weight.

17. The process as claimed in claim 16, wherein the moisture content is at most 10% by weight.

* * * * *